United States Patent

Torii et al.

[11] Patent Number: 6,011,151
[45] Date of Patent: *Jan. 4, 2000

[54] PROCESS FOR PREPARING β-LACTAM HALIDE COMPOUND

[75] Inventors: Sigeru Torii, Okayama-ken; Hideo Tanaka, Oakayama; Michio Sasaoka, Tokushima; Yutaka Kameyama, Tokushima; Daisuke Suzuki, Tokushima, all of Japan

[73] Assignee: Otsuka Kagaku Kabushiki Kaisha, Osaka, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/732,444

[22] PCT Filed: Mar. 1, 1996

[86] PCT No.: PCT/JP96/00489

§ 371 Date: Nov. 6, 1996

§ 102(e) Date: Nov. 6, 1996

[87] PCT Pub. No.: WO96/28421

PCT Pub. Date: Sep. 19, 1996

[30] Foreign Application Priority Data

Mar. 10, 1995 [JP] Japan .................... 7-079489

[51] Int. Cl.⁷ .................. C07D 205/09; C07D 205/095; C07D 205/085; C07D 205/08
[52] U.S. Cl. .................. 540/200; 540/358; 540/362; 540/363
[58] Field of Search .................. 540/200, 362, 540/363, 358

[56] References Cited

U.S. PATENT DOCUMENTS

| 5,196,530 | 3/1993 | Torii | 540/310 |
| 5,204,458 | 4/1993 | Torri | 540/222 |

FOREIGN PATENT DOCUMENTS

| 43-8084 | 3/1968 | Japan . |
| 49-18832 | 2/1974 | Japan . |
| 51-122091 | 10/1976 | Japan . |
| 52-14798 | 2/1977 | Japan . |
| 6-65252 | 3/1994 | Japan . |

OTHER PUBLICATIONS

TanakaBioorganic & Meidcinal Chemical Letters 3(11) 2253, 1993.
Baldwin, J. Chem Soc Chem Comm p. 81, Jan. 1987.

*Primary Examiner*—Mark L. Berch
*Attorney, Agent, or Firm*—Nikaido, Marmelstein, Murray & Oram LLP

[57] ABSTRACT

A process for preparing a β-lactam halide compound represented by the formula (2) characterized by halogenating the allenyl group of an allenyl β-lactam compound represented by the formula (1) with a cupric halide and a metal halide to obtain the β-lactam halide compound

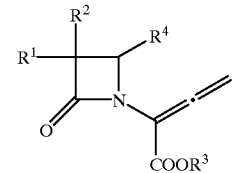
(1)

wherein $R^1$ is a hydrogen atom or amino or protected amino, $R^2$ is a hydrogen atom, halogen atom, lower alkoxyl, lower acyl, or lower alkyl having a hydroxyl group or protected hydroxyl group as a substituent, $R^3$ is a hydrogen atom or carboxylic acid protecting group, and $R^4$ is a hydrocarbon group which may have a substituent, or the group —S—S(O)n-Ar, n being 0 to 2, Ar being aryl which may have a substituent

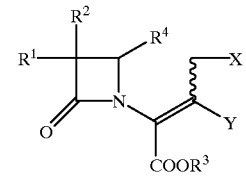
(2)

wherein $R^1$, $R^2$, $R^3$ and $R^4$ are the same as defined above, X and Y are each halogen atom.

4 Claims, No Drawings

PROCESS FOR PREPARING β-LACTAM HALIDE COMPOUND

TECHNICAL FIELD

The β-lactam halide compounds (2) to be described below are important intermediates which can be readily made into derivatives such as 3-norcephem and isocephem (Can. J. Chem., 1978, 56, 1335).

BACKGROUND ART

The β-lactam halide compound represented by the general formula (2) is prepared by reacting halogen molecules with an allenyl β-lactam compound represented by the general formula (1) below as is already known (Can. J. Chem., 1978, 56, 1335). However, this process affords a mixture of α, β-lactam and β, γ-position isomers depending on the kind of halogen molecule and is not usable in actuality. It is also reported that as shown in the diagram, a keto-form β-lactam compound is enolized into an enol ether or vinyl halide, followed by halogenation with N-bromosuccinimide or N-chlorosuccinimide in the presence of a radical generating agent (JP-A-135859/1983). Since this process requires use of a hazardous reagent for reaction, processes which are industrially more feasible are desired

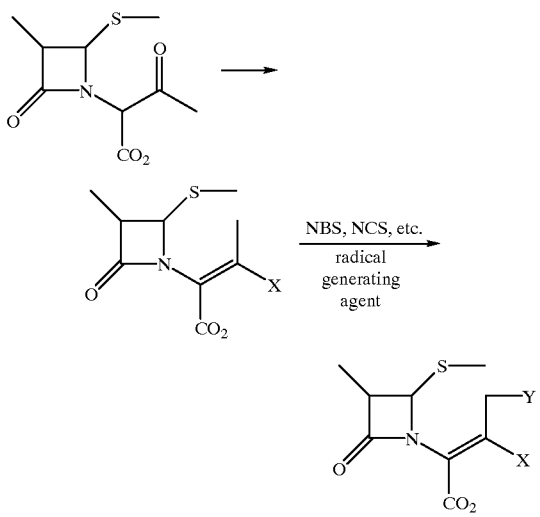

wherein the group A, group S—D and group E are groups analogous respectively to the group $R^1/R^2$, group $R^4$ and group $R^3$ of the invention to be described below.

An object of the present invention is to provide a process for preparing a β-lactam halide compound represented by the general formula (2) through a simple procedure in a high yield with a high purity using an allenyl β-lactam compound represented by the general formula (1) as the starting material, by developing a novel halogenating reagent having a high position selectivity.

DISCLOSURE OF THE INVENTION

The present invention provides a process for preparing a β-lactam halide compound represented by the formula (2) characterized by halogenating the allenyl group of an allenyl β-lactam compound represented by the formula (1) with a cupric halide and a metal halide to obtain the β-lactam halide compound

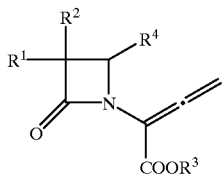

(1)

wherein $R^1$ is a hydrogen atom or amino or protected amino, $R^2$ is a hydrogen atom, halogen atom, lower alkoxyl, lower acyl, or lower alkyl having a hydroxyl group or protected hydroxyl group as a substituent, $R^3$ is a hydrogen atom or carboxylic acid protecting group, and $R^4$ is a hydrocarbon group which may have a substituent, or the group —S—S(O)n-Ar, n being 0 to 2, Ar being aryl which may have a substituent

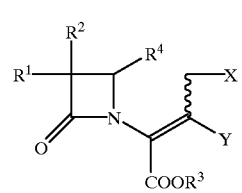

(2)

wherein $R^1$, $R^2$, $R^3$ and $R^4$ are the same as defined above, X and Y are each halogen atom.

Examples of groups mentioned herein are as follows.

Exemplary of the protected amino represented by $R^1$ are amido groups such as phenoxyacetamido, p-methylphenoxyacetamido, p-methoxyphenoxyacetamido, p-chlorophenoxyacetamido, p-bromophenoxyacetamido, phenylacetamido, p-methylphenylacetamido, p-methoxyphenylacetamido, p-chlorophenylacetamido, p-bromophenylacetamido, phenylmonochloroacetamido, phenyldichloroacetamido, phenylhydroxyacetamido, thienylacetamido, phenylacetoxyacetamido, α-oxophenylacetamido, benzamido, p-methylbenzamido, p-methoxybenzamido, p-chlorobenzamido, p-bromobenzamido, phenylglycylamido, phenylglycylamido having protected amino, p-hydroxyphenylglycylamido, p-hydroxyphenylglycylamido having protected amino and/or protected hydroxyl, etc.; imido groups such as phthalimido, nitrophthalimido, etc., in addition to the groups disclosed in Theodora W. Greene, 1981,"Protective Groups in Organic Synthesis" (hereinafter referred to merely as the "literature"), Chap. 7 (pp. 218~287). Examples of protective groups for the amino of phenylglycylamido group and p-hydroxyphenylglycylamido group are those disclosed in the literature, Chap. 7 (pp. 218~287). Examples of protective groups for the hydroxyl of p-hydroxyphenylglycylamido group are those disclosed in the literature, Chap. 2 (pp. 10~72).

Examples of halogen atom represented by $R^2$ are fluorine, chlorine, bromine or iodine atom. Exemplary of the lower alkoxyl represented by $R^2$ are straight-chain or branched $C_{1-4}$ alkoxyl groups such as methoxy, ethoxy, n-propoxy, isopropoxy, n-butoxy, isobutoxy, sec-butoxy and tert-butoxy groups.

Exemplary of the lower acyl represented by $R^2$ are straight-chain or branched $C_{1-4}$ acyl groups such as formyl, acetyl, propionyl, butyryl and isobutyryl.

Examples of protective groups for the protected hydroxyl in the lower alkyl represented by $R^2$ and substituted with hydroxyl or protected hydroxyl, and for the protected hydroxyl represented by $R^2$ are those disclosed in the literature, Chap. 2 (pp. 10~72). The substituted lower alkyl represented by $R^2$ may have as its substituent(s) one or at least two same or different groups selected from among hydroxyl and the protected hydroxyl groups. Such substituent(s) may be positioned on at least one carbon atom of the alkyl. Examples of lower alkyl are straight-chain or branched $C_{1-4}$ alkyl group such as methyl, ethyl, n-propyl, isopropyl, n-butyl, isobutyl, sec-butyl or tert-butyl.

Exemplary of the carboxylic acid protecting group represented by $R^3$ are allyl, benzyl, p-methoxybenzyl, p-nitrobenzyl, diphenylmethyl, trichloromethyl, tert-butyl, and those disclosed in the literature, Chap. 5 (pp. 152~192).

Examples of hydrocarbon groups and substituted hydrocarbon groups represented by $R^4$ are straight-chain or branched $C_{1-4}$ alkyl groups (such as methyl, ethyl, propyl, isopropyl, butyl, sec-butyl or tert-butyl), alkenyl groups (such as allyl or butenyl), $C_{3-8}$ cycloalkyl groups (such as cyclopropyl, cyclobutyl, cyclopentyl or cyclohexyl), or aromatic hydrocarbon groups (such as phenyl or naphthyl). Exemplary of the substituent which may be substituted in the hydrocarbon group are halogen atoms (such as fluorine, chlorine, bromine, iodine atom), straight-chain or branched $C_{1-4}$ alkoxyl groups (such as methoxy, ethoxy), straight-chain or branched $C_{1-4}$ alkylthio groups (such as methylthio, ethylthio), straight-chain or branched $C_{1-4}$ alkylsulfonyloxy groups (such as methanesulfonyloxy, trifluoromethanesulfonyloxy), aromatic sulfonyloxy or substituted aromatic sulfonyloxy (such as benzenesulfonyloxy, toluenesulfonyloxy), straight-chain or branched $C_{1-4}$ alkyl groups (such as methyl, ethyl), amino, amino which has as a substituent one or two straight-chain or branched $C_{1-4}$ alkyl groups (such as methylamino, dimethylamino, ethylamino, diethylamino), hydroxyl, acyloxy group represented by R'COO— wherein R' is phenyl, tolyl, or straight-chain or branched $C_{1-4}$ alkyl group (such as phenylcarbonyloxy, acetyloxy), acyl group represented by R'CO— wherein R' is as defined above (such as phenylcarbonyl, acetyl), nitro, cyano, phenyl, etc. The hydrocarbon group represented by $R^4$ may have 1 to 5, especially 1 to 3, same or different groups selected from among the above substituents.

Examples of aryl and substituted aryl represented by Ar are phenyl, naphthyl, nitrogen-containing heterocyclic group, etc. Exemplary of the nitrogen-containing heterocyclic groups are benzothiazol group, triazol group, thiazol group or tetrazol group. Exemplary of the substituent which may be substituted in the aryl group are those which may be substituted in the above hydrocarbon groups represented by $R^4$. When the aryl represented by Ar is phenyl group, the aryl may have 1 to 5, especially 1 to 3, same or different groups selected from among the above substituents. When the aryl represented by Ar is naphtyl group, the aryl may have 1 to 7, especially 1 to 3, same or different groups selected from among the above substituents.

Examples of halogen atoms represented by X, Y are fluorine, chlorine, bromine or iodine atom.

The allenyl β-lactam compound represented by the formula (1) and serving as the starting material of the invention can be produced, for example, by the following process. The desired compound (1) can be prepared by causing a β-lactam compound represented by the general formula (3) to act on a base in an inert solvent.

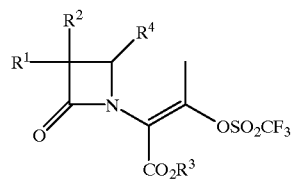

(3)

wherein $R^1$, $R^2$, $R^3$ and $R^4$ are the same as defined above.

The reaction can be conducted in a suitable solvent. Examples of solvents useful in the above reaction are alcohols such as methanol, ethanol, propanol, isopropanol, butanol and tert-butanol, lower alkyl esters of lower carboxylic acids such as methyl formate, ethyl formate, propyl formate, butyl formate, methyl acetate, ethyl acetate, propyl acetate, butyl acetate, methyl propionate and ethyl propionate, ketones such as acetone, methyl ethyl ketone, methyl propyl ketone, methyl butyl ketone, methyl isobutyl ketone and diethyl ketone, ethers such as diethyl ether, ethyl propyl ether, ethyl butyl ether, dipropyl ether, diisopropyl ether, dibutyl ether, methyl cellosolve and dimethoxyethane, cyclic ethers such as tetrahydrofuran, dioxane and dioxolan, nitriles such as acetonitrile, propionitrile, butyronitrile, isobutyronitrile and valeronitrile, substituted or unsubstituted aromatic hydrocarbons such as benzene, toluene, xylene, chlorobenzene and anisole, hydrocarbon halides such as dichloromethane, chloroform, dichloroethane, trichloroethane, dibromoethane, propylene dichloride, carbon tetrachloride and freons, aliphatic hydrocarbons such as pentane, hexane, heptane and octane, cycloalkanes such as cyclopentane, cyclohexane, cycloheptane and cyclooctane, amides such as dimethylformamide and dimethylacetamide, dimethylsulfoxide, etc. These solvents are used singly or in admixture of at least two of them. These solvents may contain water as required. These solvents are used in an amount of about 10 to about 200 liters, preferably about 20 to about 100 liters, per kilogram of the compound of the formula (3). The reaction is conducted usually at −78 ° C. to 60 ° C., preferably −40 ° C. to 30 ° C. Examples of useful base are N,N,N-tri lower alkyl amines such as trimethylamine, dimethylethylamine, triethylamine and diisopropylethylamine, N-lower alkyl azacycloalkanes such as N-methylpiperidine and N-ethylpiperidine, N-phenyl lower alkyl-N,N-di lower alkyl amines such as N-benzyl-N,N-dimethylamine and N-benzyl-N,N-diethylamine, N,N-dialkyl aromatic amines such as N,N-dimethylaniline, nitrogen-containing aromatic amines such as pyridine, bicycloamines such as diazabicycloundecene and diazabicyclononene, and a mixture of these amines. These bases are used usually in an amount of 1 to 10 equivalents based on the β-lactam compound of the formula (3). When required, it is recommended the base is added until the β-lactam compound of the formula (3) is consumed. The resulting allenyl β-lactam compound of the formula (1) can be isolated by the usual purification method but can be used in the next reaction without purification.

A cupric halide and a metal halide are caused to act on the allenyl group of the allenyl β-lactam compound represented by the formula (1) and thus obtained, whereby the compound (1) can be converted to a β-lactam halide compound represented by the formula (2).

Examples of useful cupric (II) halides include cupric (II) chloride, cupric (II) bromide and cupric (II) iodide. While various metal salts are usable as metal halides, preferable to use are halogen salts of alkali metals and alkaline earth metals. Examples of such salts include lithium chloride, lithium bromide, lithium iodide, calcium chloride, calcium bromide, calcium iodide, barium chloride, barium bromide, barium iodide, strontium chloride, strontium bromide, strontium iodide and the like. The cupric (II) halide is used usually in an amount of 1 to 10 equivalents relative to the allenyl β-lactam compound of the formula (1). When required, it is desirable to use an additional amount of the halide until the allenyl β-lactam compound of the formula (1) disappears. The metal halide is used usually in an amount of 1 to 10 equivalents relative to the β-lactam compound of the formula (1). When required, it is desirable to use an additional amount of the halide until the β-lactam compound of the formula (1) disappears. Although the proportion of the metal halide to be used varies with the valence and kind of metal halide, it is desirable to use the metal halide in 0.1 to 10 times, usually 0.3 to 3 times, the amount of the cupric (II) halide in molar ratio.

The reaction is conducted in a suitable solvent. Examples of solvents useful in the reaction are lower alkyl esters of lower carboxylic acids such as methyl formate, ethyl formate, propyl formate, butyl formate, methyl acetate, ethyl acetate, propyl acetate, butyl acetate, methyl propionate and ethyl propionate, ketones such as acetone, methyl ethyl ketone, methyl propyl ketone, methyl butyl ketone, methyl isobutyl ketone and diethyl ketone, ethers such as diethyl ether, ethyl propyl ether, ethyl butyl ether, dipropyl ether, diisopropyl ether, dibutyl ether, methyl cellosolve and dimethoxyethane, cyclic ethers such as tetrahydrofuran, dioxane and dioxolan, nitriles such as acetonitrile, propionitrile, butyronitrile, isobutyronitrile and valeronitrile, substituted or unsubstituted aromatic hydrocarbons such as benzene, toluene, xylene, chlorobenzene and anisole, hydrocarbon halides such as dichloromethane, chloroform, dichloroethane, trichloroethane, dibromoethane, propylene dichloride, carbon tetrachloride and freons, aliphatic hydrocarbons such as pentane, hexane, heptane and octane, cycloalkanes such as cyclopentane, cyclohexane, cycloheptane and cyclooctane, amides such as dimethylformamide and dimethylacetamide, dimethylsulfoxide, etc. These solvents are used singly or in admixture of at least two of them. These solvents are used in an amount of about 10 to about 200 liters, preferably about 20 to about 100 liters, per kilogram of the compound of the formula (1).

The reaction is conducted usually at −78° C. to 60° C., preferably −20° C. to 30° C. The reaction can be conducted, as required, in a sealed vessel, or at an atmosphere of an inert gas such as nitrogen gas. The resulting halogenated β-lactam compound of the formula (2) can be isolated by the usual purification method.

BEST MODE OF CARRYING OUT THE INVENTION

The present invention will be clarified in greater detail with reference to the following examples. Ph stands for $C_6H_5$—.

EXAMPLE 1

A 200 mg quantity of compound (1a) ($R^1$=PhCH$_2$CONH, $R^2$=H, $R^3$=CH$_2$C$_6$H$_4$OCH$_3$-p, $R^4$=S—SO$_2$Ph) (MW 578.7, 0.346 mmol), 200 mg of cupric chloride (MW 99.0, 2.0 mmoles) and 200 mg of calcium chloride (MW 110.99, 1.8 mmoles) were weighend out and placed into a 10-ml flask of the egg plant type, and stirred for 1 hour with addition of 2 ml of N,N-dimethylformamide. The reaction mixture was poured into 1N hydrochloric acid, followed by extraction with ethyl acetate. The extract was washed with water twice and with brine once and then dried over anhydrous sodium sulfate. The solvent was removed from the resulting extract in vacuo, and the residue was thereafter purified by silica gel column chromatography, yielding compound (2a) (X=Y=Cl) (191 mg, 85%).

$^1$H NMR(CDCl$_3$) δ: 3.58 (s, 0.3H), 3.66 (d, J=8Hz, 0.85H), 3.70 (d, J=8 Hz, 0.85H), 3.80 (s, 3H), 4.26 (d, J=14 Hz, 0.15H), 4.67 (s, 1.7H), 4.71 (d, J=14 Hz, 0.15H), 4.73 (dd, J=4, 8 Hz, 0.15H), 5.08 (d, J=12 Hz, 0.15H), 5.13 (d, J=12 Hz, 0.85H), 5.20 (d, J=12 Hz, 0.15H), 5.22 (d, J=12 Hz, 0.85H), 5.23 (dd, J=4, 8 Hz, 0.85H), 5.83 (d, J=4 Hz, 0.85H), 5.89 (d, J=4 Hz, 0.15H), 5.90 (d, J=8 Hz, 0.85H), 5.95 (d, J=8 Hz, 0.15H), 6.90~8.75(m, 14H)

EXAMPLE 2

In 6 ml of N,N-dimethylformamide was dissolved 530 mg of compound (1b) ($R^1$=phthalimido, $R^2$=H, $R^3$=CHPh$_2$, $R^4$=CH$_2$OCOCH$_3$) (MW 536.6, 0.99 mmol) 500 mg of cupric chloride (MW 99.0, 5.0 mmoles) and 500 mg of calcium chloride (MW 110.99, 4.5 mmoles) were added to the solution, and the mixture was stirred at room temperature for 1 hour. The reaction mixture was poured into 1N hydrochloric acid, followed by extraction with ethyl acetate. The extract was washed with water twice and with brine once and then dried over anhydrous sodium sulfate. The solvent was removed from the resulting extract in vacuo, and the residue was thereafter purified by silica gel column chromatography, giving compound (2b) (X=Y=Cl) (548 mg, 90%).

$^1$H NMR(CDCl$_3$) δ: 1.81 (bs, 3H), 4.18~4.60 (m, 3H), 4.36 (d, J=12 Hz, 0.3H), 4.57 (d, J=12 Hz, 0.7H), 4.87 (d, J=12 Hz, 0.7H), 5.12 (d, J=12 Hz, 0.3H), 5.53 (d, J=6 Hz, 1H), 7.03 (s, 0.3H), 7.04 (s, 0.7H), 7.22~7.56 (m, 10H), 7.75~7.91 (m, 4H)

EXAMPLE 3

In 6 ml of N,N-dimethylformamide was dissolved 559 mg of compound (1c) ($R^1$=phthalimido, $R^2$=H, $R_3$=CHPh$_2$, $R^4$=CH$_2$OSO$_2$CH$_3$) (MW 558.6, 1.00 mmol), 500 mg of cupric chloride (MW 99.0, 5.0 mmoles) and 500 mg of calcium chloride (MW 110.99, 4.5 mmoles) were added to the solution, and the mixture was stirred at room temperature for 1 hour. The reaction mixture was poured into 1N hydrochloric acid, followed by extraction with ethyl acetate. The extract was washed with water twice and with brine once and then dried over anhydrous sodium sulfate. The solvent was removed from the resulting extract in vacuo, and the residue was thereafter purified by silica gel column chromatography, giving compound (2c) (X=Y=Cl) (558 mg, 87%).

$^1$H NMR(CDCl$_3$) δ: 2.79 (s, 3H), 4.31~4.65 (m, 3H), 4.55 (d, J=12 Hz, 1H), 4.88 (d, J=12 Hz, 1H), 5.60 (d, J=6 Hz, 1H), 7.02 (s, 1H), 7.21~7.53 (m, 10H), 7.78~7.95 (m, 4H)

EXAMPLE 4

In 6 ml of N,N-dimethylformamide was dissolved 559 mg of compound (1d) ($R^1$=phthalimido, $R^2$=H, $R^3$=CHPh$_2$, $R^4$=CH$_2$OSO$_2$CH$_3$) (MW 558.6, 1.00 mmol), 500 mg of cupric bromide (MW 143.15, 3.5 mmoles) and 500 mg of calcium chloride (MW 110.99, 4.5 mmoles) were added to the solution, and the mixture was stirred at room temperature for 1 hour. The reaction mixture was poured into 1N hydrochloric acid, followed by extraction with ethyl acetate. The extract was washed with water twice and with brine once and then dried over anhydrous sodium sulfate. The solvent was removed from the resulting extract in vacuo, and the residue was thereafter purified by silica gel column chromatography, giving compound (2d) (X=Cl, Y=Br) (536 mg, 78%).

$^1$H NMR (CDCl$_3$) δ: 2.78 (s, 1.5H), 2.80 (s, 1.5H), 4.13~4.72 (m, 3.5H), 4.58 (d, J=12 Hz, 0.5H), 4.88 (d, J=12 Hz, 0.5H), 5.09 (d, J=12 Hz, 0.5H), 5.60 (d, J=6 Hz, 1H), 7.05 (s, 0.5H), 7.06 (s, 0.5H), 7.23~7.49 (m, 10H), 7.85~7.98 (m, 4H)

EXAMPLE 5

In 6 ml of N,N-dimethylformamide was dissolved 515 mg of compound (1e) (R$^1$=phthalimido, R$^2$=H, R$^3$=CHPh$_2$, R$^4$=CH$_2$Cl) (MW 513.0, 1.00 mmol), 500 mg of cupric chloride MW 99.0, 5.0 mmoles) and 500 mg of calcium chloride (MW 110.99, 4.5 mmoles) were added to the solution, and the mixture was stirred at room temperature for 1 hour. The reaction mixture was poured into 1N hydrochloric acid, followed by extraction with ethyl acetate. The extract was washed with water twice and with brine once and then dried over anhydrous sodium sulfate. The solvent was removed from the resulting extract in vacuo, and the residue was thereafter purified by silica gel column chromatography, giving compound (2e) (X=Y=Cl) (432 mg, 74%)

$^1$H NMR(CDCl$_3$) δ:3.52~4.50 (m, 3.4H), 4.62 (d, J=12 Hz, 0.6H), 4.81 (d, J=12 Hz, 0.6H), 5.08 (d, J=12 Hz, 0.4H), 5.52 (d, J=6 Hz, 0.4H), 5.55 (d, J=6 Hz, 0.6H), 7.03 (s, 0.4H), 7.05 (s, 0.6H), 7.21~7.49 (m, 10H), 7.75~7.97 (m, 4H)

EXAMPLE 6

In 6 ml of N,N-dimethylformamide was dissolved 603 mg of compound (1f) (R$^{1=4}$-nitrophthalimido, R$^2$=H, R$^3$=CHPh$_2$, R$^4$=CH$_2$OSO$_2$CH$_3$) (MW 603.6, 1.00 mmol), 500 mg of cupric chloride (MW 99.0, 5.0 mmoles) and 500 mg of calcium chloride (MW 110.99, 4.5 mmoles) were added to the solution, and the mixture was stirred at room temperature for 1 hour. The reaction mixture was poured into 1N hydrochloric acid, followed by extraction with ethyl acetate. The extract was washed with water twice and with brine once and then dried over anhydrous sodium sulfate. The solvent was removed from the resulting extract in vacuo, and the residue was thereafter purified by silica gel column chromatography, giving compound (2f) (X=Y=Cl) (548 mg, 80%).

$^1$H NMR(CDCl$_3$) δ: 2.78 (s, 1.5H), 2.80 (s, 1.5H), 4.22~4.74 (m, 4H), 4.84 (d, J=12 Hz, 0.5H), 5.05 (d, J=12 Hz, 0.5H), 5.61 (d, J=6 Hz, 1H), 7.03 (s, 0.5H), 7.06 (s, 0.5H), 7.21~7.55 (m, 10H), 8.10 (d, J=3 Hz, 1H), 8.63 (d, J=3 Hz, 1H), 8.70 (bs, 1H)

EXAMPLE 7

In 6 ml of N,N-dimethylformamide was dissolved 582 mg of compound (1g) (R$^1$=4-nitrophthalimido, R$^2$=H, R$^3$=CHPh$_2$, R$^4$=CH$_2$OCOCH$_3$) (MW 581.6, 1.00 mmol), 500 mg of cupric chloride (MW 99.0, 5.0 mmoles) and 500 mg of calcium chloride (MW 110.99, 4.5 mmoles) were added to the solution, and the mixture was stirred at room temperature for 1 hour. The reaction mixture was poured into 1N hydrochloric acid, followed by extraction with ethyl acetate. The extract was washed with water twice and with brine once and then dried over anhydrous sodium sulfate. The solvent was removed from the resulting extract in vacuo, and the residue was thereafter purified by silica gel column chromatography, giving compound (2g) (X=Y=Cl) (458 mg, 80%).

$^1$H NMR(CDCl$_3$) δ: 1.79 (s, 0.7H), 1.82 (s, 0.3H), 4.19~4.58 (m, 3.3H), 4.59 (d, J=12 Hz, 0.7H), 4.85 (d, J=12 Hz, 0.7H), 5.08 (d, J=12 Hz, 0.3H), 5.49 (d, J=6 Hz, 0.7H), 5.53 (d, J=6 Hz, 0.3H), 7.00 (s, 0.7H), 7.04 (s, 0.3H), 7.21~7.48 (m, 10H), 8.11 (d, J=3 Hz, 1H), 8.67~8.73 (m, 2H)

Reference Example 1

When potassium acetate is reacted in DMF with compound (2c) obtained by the reaction of Example 3 according to the process disclosed in Can. J. Chem., 56, 2879 (1978), the reaction affords 3-acetoxymethylisocephem compound (4). This compound can be converted to a compound having physiological activity by the process disclosed in Can. J. Chem., 58, 2508 (1980), that is, by introducing a required substituent (e.g. tetrazolethio group) into the compound at its 3'-position, deprotecting the 7-position, introducing required acyl group to the resulting compound at the 7-position and deprotecting ester site at the 3-position.

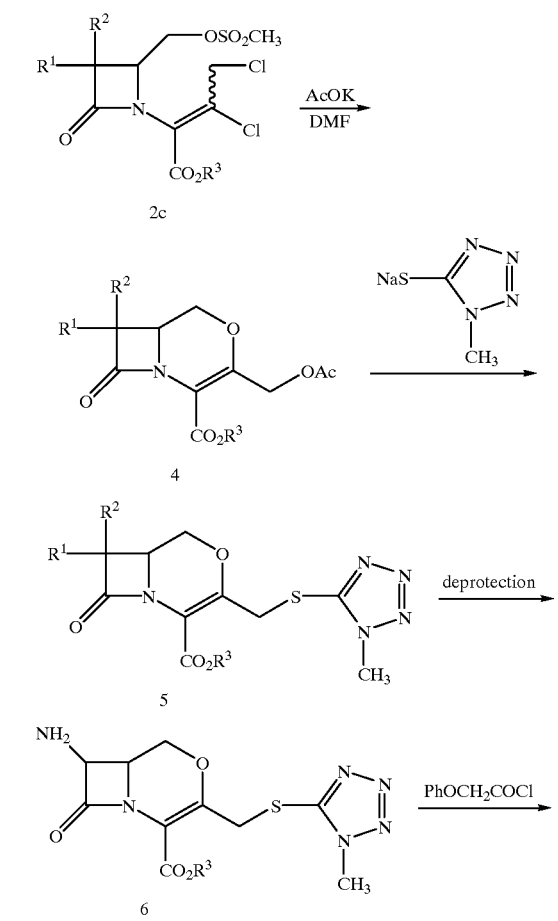

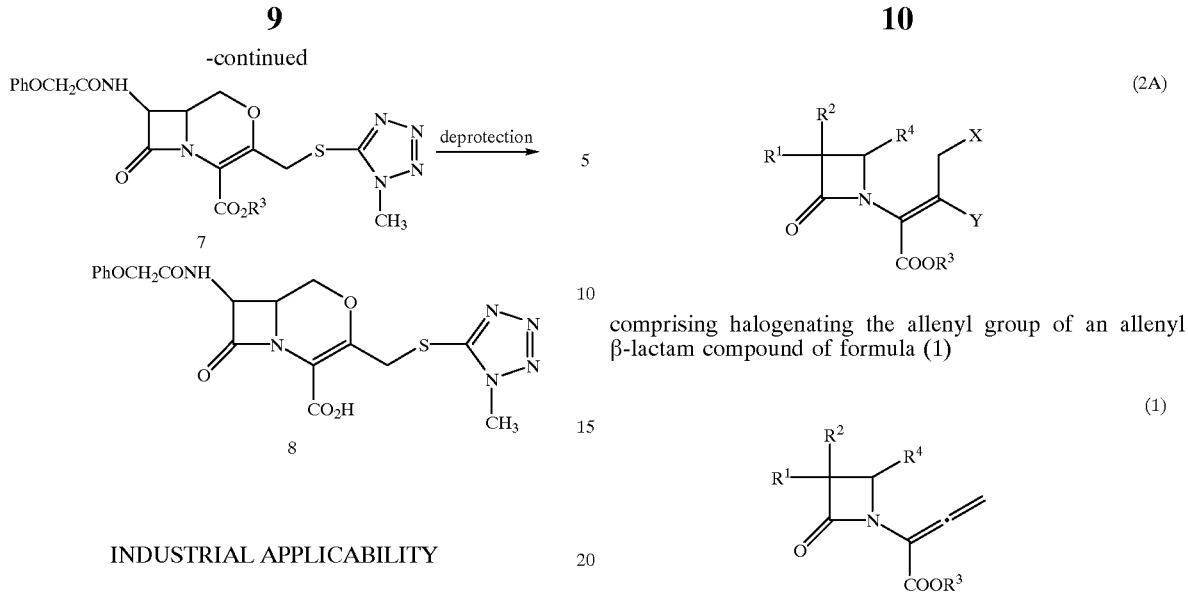

INDUSTRIAL APPLICABILITY

According to the present invention, it is obtained a process for preparing a β-lactam halide compound represented by the general formula (2) through a simple procedure in a high yield with a high purity using an allenyl β-lactam compound represented by the general formula (1) as the starting material, by developing a novel halogenating reagent having a high position selectivity.

The present reaction per se is a novel reaction, making it possible to position-selectively halogenate allene compounds with the combination of a cupric halide and a metal halide. Whereas it has been impossible to replace X and Y by different halogen atoms position-selectively, even such different halogen atoms desired can be introduced position-selectively by the present reaction.

We claim:
1. A process for preparing a β-lactam halide compound represented by the formula 2A comprising halogenating the allenyl group of an allenyl β-lactam compound of formula (1)

with a cupric (II) halide and a metal halide to obtain the β-lactam halide compound, wherein $R^1$ is an amino or a protected amino, $R^2$ is a hydrogen atom, $R^3$ is a hydrogen atom or carboxylic acid protecting group, and $R^4$ is selected from the group consisting of —$CH_2OSO_2CH_3$ and —$CH_2OSO_2CF_3$ wherein formula 2A has $R^1$, $R^2$, $R^3$, and $R^4$ as defined above, and X and Y are each halogen atoms.

2. The process of claim 1, wherein said cupric (II) halide is selected from the group consisting of cupric (II) chloride, cupric (II) bromide and cupric (II) iodide.

3. The process of claim 1, wherein the metal halide is a halogen salt of an alkali metal or alkaline earth metal.

4. The process of claim 3, wherein the metal halide is selected from the group consisting of lithium chloride, lithium bromide, lithium iodide, calcium chloride, calcium bromide, calcium iodide, barium chloride, barium bromide, barium iodide, strontium chloride, strontium bromide and strontium iodide.

* * * * *